(12) United States Patent
Neuberger

(10) Patent No.: US 6,758,844 B2
(45) Date of Patent: Jul. 6, 2004

(54) SYSTEM AND METHOD FOR ORAL TREATMENTS

(75) Inventor: Wolfgang Neuberger, Labuan (MY)

(73) Assignee: CeramOptec Industries, Inc., East Longmeadow, MA (US)

(*) Notice: Subject to any disclaimer, the term of this patent is extended or adjusted under 35 U.S.C. 154(b) by 0 days.

(21) Appl. No.: 10/056,130

(22) Filed: Jan. 24, 2002

(65) Prior Publication Data
US 2003/0139735 A1 Jul. 24, 2003

(51) Int. Cl.⁷ ............................................. A61B 18/22
(52) U.S. Cl. ............................................. 606/3; 606/10
(58) Field of Search .................... 606/2, 3, 10, 13, 606/14, 15

(56) References Cited

U.S. PATENT DOCUMENTS

| | | | |
|---|---|---|---|
| 5,290,274 A | | 3/1994 | Levy et al. |
| 5,318,562 A | * | 6/1994 | Levy et al. ............. 606/16 |
| 5,374,266 A | | 12/1994 | Kataoka et al. |
| 5,458,594 A | * | 10/1995 | Mueller et al. ............. 606/15 |
| 5,825,958 A | * | 10/1998 | Gollihar et al. ............. 604/14 |
| 5,885,082 A | * | 3/1999 | Levy ............. 606/15 |
| 6,129,721 A | | 10/2000 | Kataoka et al. |
| 6,267,779 B1 | * | 7/2001 | Gerdes ............. 607/89 |
| 6,350,123 B1 | * | 2/2002 | Rizoiu et al. ............. 606/10 |

FOREIGN PATENT DOCUMENTS

WO  WO 99/39652  8/1999

OTHER PUBLICATIONS

Therapeutic Guidelines for Diode Laser Applications in Medicine□□Laser– und Medizin–Technologie GmbH, LMTB, Berlin, Aug. 1997.*

Institute For Laser Dentistry web page dated Feb. 3, 2001. http://web.archive.org/web/20010203190800/www.laser-dentistry.ca/index2.html.*

Romanos et al., "Effects of Diode and Nd:YAG Laser Irradiation on Titanium Discs: A Scanning Electron Microscope Examination", Journal of Periodontology, 2000, 810–815, 71, American Academy of Periodontology, US.

* cited by examiner

Primary Examiner—Roy D. Gibson
Assistant Examiner—Henry M. Johnson, III
(74) Attorney, Agent, or Firm—BJ Associates; Bolesh J. Skutnik

(57) ABSTRACT

A system and method is disclosed for improved treatment of oral tissues using 980 nm laser radiation and a handpiece with means for concurrently delivering the laser radiation and a liquid/gas spray onto the treatment area to improve the treatment effects. Unwanted heating and carbonization of surrounding tissues is reduced. The liquid/gas spray may be mixed inside the handpiece or in a separate device. The combination of cooling sprays with radiation wavelengths having high absorption in water has previously been avoided due to the thought that energy absorption by the cooling fluid would render the energy delivered to the tissue uncontrollable and of minimal benefit. Preferably, pulsed laser light provides a localized energy deposition and heating to avoid unwanted heating of underlying tissue. The liquid spray flushes away tissue debris in addition to cooling the treated tissue.

11 Claims, 2 Drawing Sheets

SYSTEM AND METHOD FOR ORAL TREATMENTS

BACKGROUND OF THE INVENTION

1. Field of the Invention

The present invention relates to the field of treatment of oral tissues using laser radiation of an especially effective wavelength and having a handpiece with means for delivery of this laser radiation and for spraying a liquid/gas mixture onto the treatment area to improve the treatment effects.

2. Information Disclosure Statement

A variety of laser treatments are used in the field of oral and maxillofacial surgery. Such treatments offer many advantages, especially because of their high coagulation properties, high incision quality, and post-operative benefits for the surgeon and the patient.

Depending on the wavelength, energy levels and radiation patterns used, the effects of laser radiation on tissue are significantly different. It is a goal of the present invention to achieve fast, non-carbonized, aesthetic surgical effects, with a limited coagulation zone in a largely non-traumatic manner with minimal or no bleeding.

During treatment, laser light heats tissue due to the absorption of energy by water molecules in the tissue, thereby destroying living cells and resulting in coagulation of the tissue for excisions or incisions. During treatment, it is essential to avoid overheating or damaging surrounding tissue and to control the effects of the radiation. The deeper the radiation penetrates the tissue, the less controllable are the resulting heat effects. Residual heat may affect the nerve of the tooth causing pain to the patient and may cause tissue to carbonize and become necrotic. Thus, it is desirable to minimize transmission of conducted heat to underlying and surrounding tissue. It is therefore desirable to accurately control the amount of light energy transferred to the tissue to be treated. The amount of energy must be sufficiently controlled so that local tissue is effectively treated and surrounding tissue is not heated by residual energy.

In WO 99/39652, it is described how to treat periodontal pockets with laser light without heating the surrounding tissue by spraying a coolant of mixed water and air onto the tissue. The device used comprises a handpiece with a combined water and fiber duct whereby the spray is generated at the output end of the handpiece. However, this disclosure does not teach how to avoid unwanted heating of deeper tissue layers. Moreover, the invention provides for conducting the laser delivery fiber and the water in one duct. This configuration is disadvantageous because the water at the fiber tip absorbs laser energy and thus renders the energy delivered to the tissue undeterminable, and moreover, the tip heats up and can cause unwanted burnings. Further the position of the fiber and therefore the aiming of the laser light is not defined. Also, WO 99/39652 mandates the use of a "wavelength that is moderately absorbed in water". The invention claims the use of wavelengths ranging from 1–1.2 microns or 1.06 to 1.07 microns, which are moderately absorbed in water. Using wavelengths that are more highly absorbed in water would presumably lower the effectiveness of the treatment and is therefore avoided.

U.S. Pat. No. 5,374,266 describes a laser device consisting of a handpiece with a special fiber and fiber duct for small cavities and uniform irradiation. This device features a cooling fluid spray that is fed along the fiber probe to clean the treatment area and cool the fiber probe after irradiation or to cool the probe during irradiation. The water is then blown peripherally from the probe so as to avoid any moisture damage to the probe fiber. Thus, the use of water in this invention is for cooling the probe, not the treatment site during irradiation.

In general, the prior art has contemplated the use of cooling liquid or sprays in conjunction with irradiation treatments to avoid thermally damaging surrounding tissues. However, only certain wavelengths have been described as effective for use in conjunction with liquid cooling means. Those wavelengths are those that are not highly absorbed in water. Indeed, as seen in WO 99/39652, the prior art contemplates the use of wavelengths, such as those on the order of 1 micron, that have relatively low absorption in water so as not to inhibit treatment. In addition, U.S. Pat. No. 6,129,721, although describing an irradiation handpiece featuring a fiber and delivery means for spraying fluid and gas that would at first seem similar to the present invention, limits its invention to those wavelengths between 1 and 5.5 microns.

U.S. Pat. No. 5,290,274 by Levy et al. describes the use of radiation with two different wavelengths in conjunction with a step of directing cooling fluid to the treatment site during irradiation. The first wavelength is between 0.7 and 1 micron, and the second wavelength is in the vicinity of 3 microns. Levy claims that the use of Nd:YAG radiation in combination with a liquid cooling source is effective, because fundamental frequency radiation with a wavelength of 1.06 microns and frequency doubled radiation with a 0.532 micron wavelength are essentially not absorbed in water. However, according to Levy, the effectiveness of an Er:YAG laser is considerably reduced when used in conjunction with a cooling liquid spray because it produces radiation of a wavelength that is highly absorbed by water.

As can be seen by the above-described prior art, the prior art teaches that the use of a wavelength that is highly absorbed by water, such as a 980 nm laser, in conjunction with a liquid cooling spray would be ineffective.

The present invention addresses the above mentioned drawbacks of the prior art by providing a method and system that avoids unwanted heating of surrounding tissue by different means and provides a very precise incision quality by a combination of laser light of a wavelength of approximately 980 nm and a cooling liquid spray. Preferably, pulsed laser light is used to provide localized energy deposition and heating, therefore avoiding unwanted heating of underlying tissue. Additional liquid spray flushes away tissue debris and provides additional cooling of treated tissue.

OBJECTIVES AND BRIEF SUMMARY OF THE INVENTION

An object of the present invention is to provide a system and method for improved treatment of oral tissue using laser light and without heating the surrounding tissue and without carbonization.

Another object of the present invention is to avoid unwanted tissue heating and significantly improve treatment results by using an advantageous wavelength for irradiation and by spraying a liquid/gas mixture onto the tissue.

Still another object of the present invention is to use laser light of a wavelength of 980 nm.

Yet another object of the present invention is to provide a handpiece with a laser fiber duct and liquid/gas ducts.

A further object of the present invention is to provide a handpiece with a changeable sterile fiber tip.

Briefly stated, the present invention provides a system and method for improved treatment of oral tissues using 980 nm laser radiation and a handpiece with means for concurrently delivering the laser radiation and a liquid/gas spray onto the treatment area to improve the treatment effects. Unwanted heating and carbonization of surrounding tissues is reduced. The liquid/gas spray may be mixed inside the handpiece or in a separate device. The combination of cooling sprays with radiation wavelengths having high absorption in water has previously been avoided due to the thought that energy absorption by the cooling fluid would render the energy delivered to the tissue uncontrollable and of minimal benefit. Preferably, pulsed laser light provides a localized energy deposition and heating to avoid unwanted heating of underlying tissue. The liquid spray flushes way tissue debris in addition to cooling the treated tissue.

The above, and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

Figure 1:
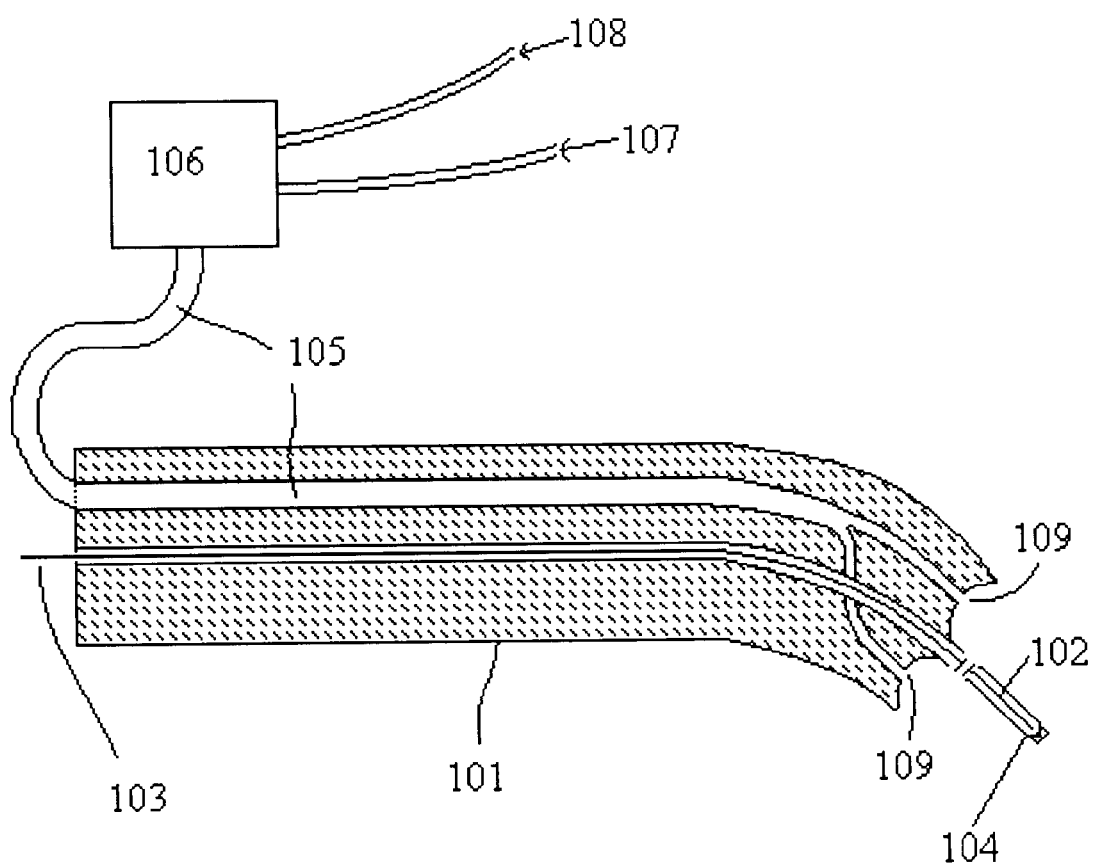
FIG. 1—handpiece with one spray duct and changeable fiber tip

The energy delivered to the tissue during laser therapy is defined by several parameters such as power density, radiation duration and wavelength. Laser wavelengths of 2 or 3 $\mu$m, 1064 nm, 980 nm or 810 nm are all used for dental applications. The 980 nm laser was found to be advantageous when compared to treatments applying other wavelengths, because the 980 nm wavelength seems to offer a unique balance between the desired level of water absorption and limited penetration depth. The water absorption curve shows a local maximum at the wavelength of 980 nm which indicates that 980 nm radiation is well absorbed by water. Additionally, because 980 nm radiation is also well absorbed in hemoglobin and oxyhemoglobin, irradiation with a 980 nm laser results in a superior tissue cutting and coagulation effect that is accomplished optically rather than thermally, unlike other wavelengths currently used. Shorter wavelengths have a lower water absorption and thus penetrate too deeply. Longer wavelengths (such as that produced by an Er:YAG) are not well absorbed in blood components such as hemoglobin and oxyhemoglobin, and are much more difficult to deliver because suitable optical fibers for transmission are not available and commonly used mirror arms are not easy to handle. Also, longer wavelengths such as those produced by Nd:YAG lasers [1064 nm] exhibit low water and blood component absorption and unacceptably high depth penetration.

Moreover, the 980 nm wavelength has the additional advantage of having a lower penetration depth than in commonly used wavelengths such as visible wavelengths or 1064 nm, and can thereby avoid undesired and uncontrolled heating of deeper tissue layers. Coagulation with 980 nm laser radiation can be controlled very precisely. Postoperative advantages such as lack of swelling, bleeding, pain, or scar tissue formation and good wound healing, are observed in all clinical applications.

This wavelength can also be used to uncover submerged implants to treat peri-implantitis without damaging the surface of the implants as it is the case with longer wavelengths or other methods (Romanos, Everts, Nentwig, "Effects of Diode and Nd:YAG Laser Irradiation on Titanium Discs: A Scanning Electron Microscope Examination", J Periodontol 2000, 71, 810–815 (2000)). When pulsed, very high energies can be applied to a small and defined treatment site to enhance the effectiveness of the treatment. The pulsed mode is especially advantageous for avoiding unwanted heating of healthy tissue because the irradiation period is shorter than the time it takes for the transport of heat into deeper tissue layers to begin. However, it has been determined that certain power levels must not be exceeded with this wavelength.

Surprisingly, and contrary to the teachings of the prior art, the additional application of a liquid/gas spray improved the results of treatment with 980 nm radiation significantly. The use of a spray has been described for treatments with other wavelengths but has not been used with 980 nm due to the high absorption of this wavelength by water relative to other wavelengths. The use of a water spray was initially expected to lead to energy losses and reduced effectiveness of the treatment. However, it has been found that this is not the case. The spray acts as a cooling means for preventing unwanted tissue heating and for keeping the incised tissue wet to prevent drying and carbonization. Further, the liquid/gas spray has the additional benefit of removing tissue debris produced by the treatment that would potentially absorb irradiation and cause carbonisation on the tissue as well as on the fiber tip. Therefore, the spray has to intersect with the fiber tip on the plane of the treatment site to achieve enhanced results.

The combined advantageous wavelength of 980 nm and liquid/gas spray provide excellent surgical and aesthetic results in various oral applications. Specific examples of these results, including a lack of swelling, bleeding, pain, or scar tissue formation and good wound healing, have been observed in all clinical applications. Among the potential clinical applications for the present invention are treatments of periodontitis, peri-implantitis, implant recovery, endodontia, hyperplasia, vestibular plastic, and incision in oral surgery. The aesthetic outcome of the method of the present invention due to a limited coagulation zone and a lack of scar tissue formation or receding tissue is of importance for such treatments as surgical treatment of the gum line at crowns. With treatments other than the present invention, the tissue recedes after the surgery thereby rendering metal or other support structures of the crown/implant visible and thus compromising the aesthetic result of the treatment.

The present invention provides a system and method for an improved treatment of oral tissue. The system includes a radiation source such as a laser emitting the advantageous wavelength of 980 nm and a delivery device for the radiation and the liquid/gas spray. The term "liquid/gas spray" may denote either a spray incorporating some combination of a liquid and a gas, or may denote a spray consisting entirely of one or more liquids. A handpiece directs the radiation and the spray to the treatment site. The shape of the handpiece can be formed in many different ways to allow the practitioner to comfortably work at several treatment sites. In a preferred embodiment, the delivery device consists of a handpiece incorporating a fiber duct and means to conduct liquid and gas. The fiber duct contains one or more optical fibers to deliver 980 nm radiation to a treatment site. Alternatively, additional wavelengths could be delivered through the duct via separate optical fibers. For example, an additional fiber could be added to deliver visible radiation that would give the user greater visibility, or to deliver radiation of a wavelength suitable for biostimulation or wound healing.

In a preferred embodiment shown in FIG. 1, handpiece 101 features disposable fiber tip 102 that can be changed in order to use new and sterilized fibers for every patient. The connection of changeable fiber tip 102 with fiber 103 in the handpiece is designed in a way that radiation is efficiently transferred, preferably by direct contact of the surfaces of the fibers. The duct for the fiber tip is short in order to avoid damaging the fiber during insertion. Preferably the fiber tip is stored with protecting cap 104 to maintain sterility of the tip before it is removed prior to treatment.

The liquid/gas spray is conducted as a spray through the handpiece in one duct 105 and originating in spraying device 106. Spraying device 106 may contain a fixed gas and liquid mixture or, as seen in FIG. 1, can be fed variable amounts through liquid feeding means 107 and gas feeding means 108. In this way, the liquid amount and flow rate as well as the gas pressure are individually controllable to produce a spray consisting of a controllable ratio of liquid to gas or to produce a spray that is purely liquid. In another embodiment, the handpiece is provided with separate ducts for gas and liquid respectively, which are then combined within the handpiece and released through nozzles 109 as a liquid/gas mixture. In either embodiment, the handpiece is provided with at least two nozzles 109 to assure uniform spraying onto the tissue. In a preferred embodiment, three nozzles are used to deliver the cooling means.

Figure 2:
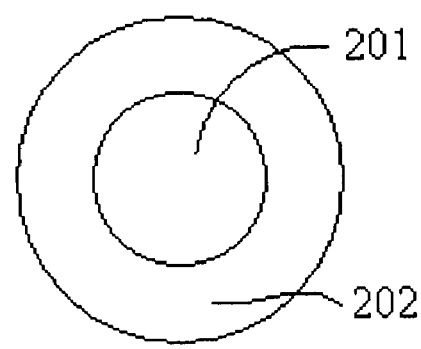
FIG. 2—fiber with ducts
Figure 2:
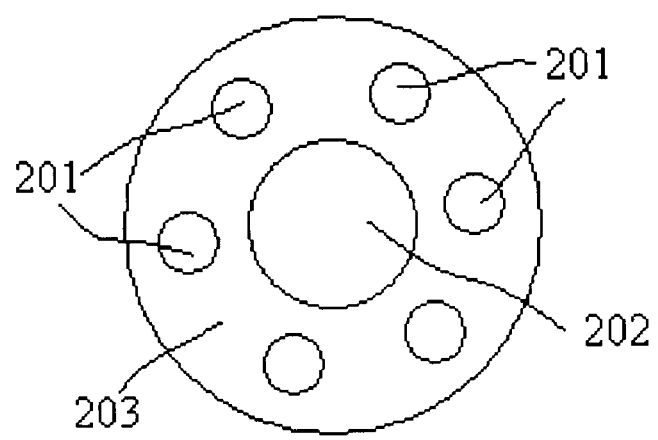

In another preferred embodiment, illustrated in FIG. 2, liquid/gas conducting duct 201 within the fiber is located coaxially with the fiber either in the center of the fiber with the radiation being conducted in outer ring 202 (FIG. 2a), or with liquid/gas duct 201 in cladding 203 surrounding fiber core 202 (FIG. 2b). The liquid gas mixture preferably is a mixture of air and water or physiologic salt solutions or disinfecting fluids. Also other inert gases like nitrogen can be used to generate the spray.

In another embodiment the handpiece can be sterilized, and especially the fiber tip is replaceable, so that new sterilized fiber tips can be inserted into the handpiece for every new treatment.

The system and method provided by the invention can successfully be used for several applications in oral surgery, e.g. periodontitis, peri-implantitis, implant recovery, endodontia, hyperplasia, vestibular plastic, incision in oral surgery.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A system for improved treatment of oral tissue comprising:

a radiation source emitting at a wavelength of about 980 nm;

a means for delivering radiation with a wavelength of about 980 nm;

an optical fiber containing at least one duct for a liquid/gas spray, which is generated from a liquid and a gas in a separate device, to deliver said radiation and said liquid/gas spray; and a handpiece which directs said radiation and a liquid/gas spray onto said tissue.

2. The system according to claim 1, wherein said handpiece comprises at least two ducts for said gas and liquid, and both being mixed within the handpiece to generate a spray.

3. The system according to claim 1, wherein said optical fiber has a central core and a cladding, and said at least one duct for said spray is located coaxially within said central core of said optical fiber.

4. The system according to claim 1, wherein said optical fiber has a core and a adding, and said at least one duct for said spray is located coaxially within the cladding of said optical fiber.

5. The system according to claim 1, wherein said handpiece comprises a replaceable fiber tip.

6. The system according to claim 1, wherein a liquid in said liquid/gas spray is selected from a group consisting of water, physiologic salt solutions and disinfecting liquids.

7. The system according to claim 1, wherein a gas in said liquid/gas spray is selected from a group consisting of air, nitrogen, and inert gases.

8. A method for treatment of oral tissue using laser radiation that reduces undesired heating and carbonization of the surrounding tissue comprising the steps of:

a) irradiating an oral tissue treatment site with radiation of a wavelength of about 980 nm using an optical fiber to direct said radiation to said treatment site, b) mixing a liquid and a gas to form a liquid/gas mixture, and c) spraying said a liquid/gas mixture, through at least one duct which is present within said optical fiber, onto said tissue during said irradiating step, wherein said irradiating and said spraying are substantially, concurrently performed through a single handpiece.

9. The method according to claim 8, wherein said mixing occurs in a separate device.

10. The method according to claim 8, wherein said mixing occurs within said handpiece.

11. The method according to claim 8, wherein said treatment of oral tissue is selected from a group insisting of oral surgery, treatment of periodontitis, peri-implantitis, implant recovery, endodontia, hyperplasia, vestibular plastic, and incision in oral surgery.

* * * * *